US007639778B2

(12) United States Patent
Kashiwagi

(10) Patent No.: US 7,639,778 B2
(45) Date of Patent: Dec. 29, 2009

(54) MAMMOGRAPHIC APPARATUS, BREAST COMPRESSION PLATE, AND BREAST FIXING METHOD

(75) Inventor: Nobuhiko Kashiwagi, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/865,025

(22) Filed: Sep. 30, 2007

(65) Prior Publication Data

US 2008/0080668 A1 Apr. 3, 2008

(30) Foreign Application Priority Data

Sep. 29, 2006 (JP) ............................ 2006-268952

(51) Int. Cl.
*A61B 6/04* (2006.01)
(52) U.S. Cl. ...................... 378/37; 378/180; 378/208
(58) Field of Classification Search .................. 378/37, 378/180, 208
See application file for complete search history.

(56) References Cited

U.S. PATENT DOCUMENTS

| 5,029,193 | A | | 7/1991 | Saffer |
| 5,050,197 | A | | 9/1991 | Virta et al. |
| 5,506,877 | A | * | 4/1996 | Niklason et al. ............... 378/37 |
| 5,594,769 | A | * | 1/1997 | Pellegrino et al. ............. 378/37 |
| 5,706,327 | A | | 1/1998 | Adamkowski et al. |
| 5,820,552 | A | * | 10/1998 | Crosby et al. ............... 600/407 |
| 6,577,703 | B2 | | 6/2003 | Lindstrom et al. |
| 6,999,553 | B2 | * | 2/2006 | Livingston ..................... 378/37 |
| 7,142,631 | B2 | * | 11/2006 | Galkin ......................... 378/37 |
| 2007/0280412 | A1 | * | 12/2007 | Defreitas et al. ............... 378/37 |

FOREIGN PATENT DOCUMENTS

JP 2004-154409 A 6/2004

* cited by examiner

*Primary Examiner*—Irakli Kiknadze
*Assistant Examiner*—Thomas R Artman
(74) *Attorney, Agent, or Firm*—Sughrue Mion, PLLC

(57) ABSTRACT

A mammographic apparatus is set to take a medio-lateral oblique view (MLO) of a breast with an arm being tilted. After having positioned the breast on an image capturing base, the radiological technician moves a breast compression plate, which is tilted with respect to the image capturing base, toward the image capturing base. When the breast compression plate abuts against the breast and the breast is braced from below by the image capturing base, the radiological technician removes a hand from between the image capturing base and the breast compression plate, and then further moves the breast compression plate toward the image capturing base. A compression plate support mechanism turns the breast compression plate to make it substantial parallel to the image capturing base, thereby positioning the breast.

18 Claims, 17 Drawing Sheets

MAMMOGRAPHIC APPARATUS, BREAST COMPRESSION PLATE, AND BREAST FIXING METHOD

BACKGROUND OF THE INVENTION

1. Field of the Invention

The present invention relates to a mammographic apparatus of capturing radiation image information of a breast, and a breast compression plate for compressing a breast and a breast fixing method for fixing a breast when an image of the breast is captured by the mammographic apparatus.

2. Description of the Related Art

In the medical field, there have widely been used radiation image capturing apparatus for applying a radiation emitted from a radiation source to a subject, and guiding the radiation that has passed through the subject to a solid-state detector or a stimulable phosphor panel, thereby recording radiation image information of the subject.

The solid-state detector includes a solid-state detecting unit which comprises a matrix of charge collecting electrodes formed on an insulating substrate and a radiation conductor disposed on the charge collecting electrodes for generating electric charges depending on the radiation that is applied to the radiation conductor. The electric charges generated by the radiation conductor and representing radiation image information are collected by the charge collecting electrodes and temporarily stored in an electric storage unit. The collected electric charges are converted into an electric signal, which is output from the solid-state detector.

The stimulable phosphor panel is a panel coated with a stimulable phosphor which, when exposed to an applied radiation, stores part of the energy of the radiation, and, when subsequently exposed to applied stimulating light such as laser beam or the like, emits light in proportion to the stored energy of the radiation. The radiation image information can be read from the stimulable phosphor panel by photoelectrically converting stimulated light that is emitted from the stimulable phosphor panel.

One of the radiation image capturing apparatus is known as a mammographic apparatus for use in breast cancer screening. The mammographic apparatus comprises an image capturing base for supporting a breast of a subject, the image capturing base incorporating a panel-shaped solid-state detector, a breast compression plate disposed opposite the image capturing base for pressing the breast against the image capturing base, and a radiation source for applying a radiation through the breast compression plate to the breast.

For capturing appropriate radiation image information of the breast, it is necessary to place the region to be imaged of the breast, which ranges from the chest wall of the subject to the nipple of the breast, properly in a predetermined range on the image capturing base.

U.S. Pat. No. 6,577,703 discloses an X-ray mammography apparatus wherein a breast compression plate is swingably supported by a rubber bushing, so that the breast compression plate follows the shape of a breast when the breast compression plate compresses the breast.

U.S. Pat. No. 5,706,327 discloses a mammographic compression apparatus wherein a breast compression plate is angularly movable about an axis substantially parallel to the chest wall of a subject. After the breast is compressed to a certain degree by the breast compression plate, a nipple end of the breast compression plate is angularly moved downwardly about the axis to compress the breast, particularly the mammary gland thereof.

U.S. Pat. Nos. 5,050,197 and 5,029,193 disclose mammographic apparatus wherein a breast compression plate has a chest end inclined downwardly. After a portion of a breast near the chest is compressed by the chest end of the breast compression plate, a nipple end of the breast compression plate is displaced toward an image capturing base to make the breast compression plate substantially horizontal.

According to U.S. Pat. Nos. 6,577,703 and 5,706,327, however, when the operator presses the breast compression plate against the breast while holding and positioning the breast with a hand, the breast compression plate is held against a wide area of the breast by following the shape of the breast. Therefore, after having pressed the breast compression plate against the breast, the operator finds it difficult to remove the hand, and may cause the breast to be displaced in position when removing the hand.

According to U.S. Pat. Nos. 5,050,197 and 5,029,193, in an initial phase of the process of compressing the breast, the portion of the breast near the chest is compressed by the chest end of the breast compression plate, whereas the other portion of the breast is free at the nipple end of the breast compression plate. Accordingly, after the breast is positioned on the image capturing base, the operator finds it easy to remove the hand.

However, as the portion of the breast near the nipple is not held by the breast compression plate in the initial phase of the breast compressing process, the portion of the breast near the nipple may possibly be displaced in position in the image capturing session.

Mammographic apparatus are capable of capturing various images of a breast, including a cranio-caudal view (CC) taken from above, a medio-lateral view (ML) taken outwardly from the center of the chest, or a medio-lateral oblique view (MLO) taken from an oblique view.

When the image capturing base and the breast compression plate are set to position the breast for capturing a medio-lateral view or a medio-lateral oblique view thereof, since the portion of the breast near the nipple is not held by the breast compression plate in the initial phase of the breast compressing process, as shown in FIG. 17 of the accompanying drawings, the portion of the breast 3 near the nipple tends to droop by gravity with respect to the predetermined range 2 on the image capturing base 1. As a result, the breast 3 is not positioned in an appropriate image capturing position.

Even if the operator holds and positions the breast with a hand, since the operator has to remove the hand at the time the breast compression plate approaches the image capturing base, the breast is liable to be displaced in position at this time.

SUMMARY OF THE INVENTION

It is a general object of the present invention to provide a mammographic apparatus, a breast compression plate, and a breast fixing method which are capable of positioning a breast easily and accurately in an appropriate position while reducing assistive actions to position the breast.

A major object of the present invention is to provide a mammographic apparatus, a breast compression plate, and a breast fixing method which are capable of positioning a breast accurately in an appropriate position regardless of an image capturing process that is employed.

Another object of the present invention is to provide a mammographic apparatus, a breast compression plate, and a breast fixing method which are capable of positioning a portion of a breast near the nipple thereof highly accurately.

Still another object of the present invention is to provide a mammographic apparatus, a breast compression plate, and a breast fixing method which allow the operator to remove a hand thereof easily from a position to hold a breast after having positioned the breast.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
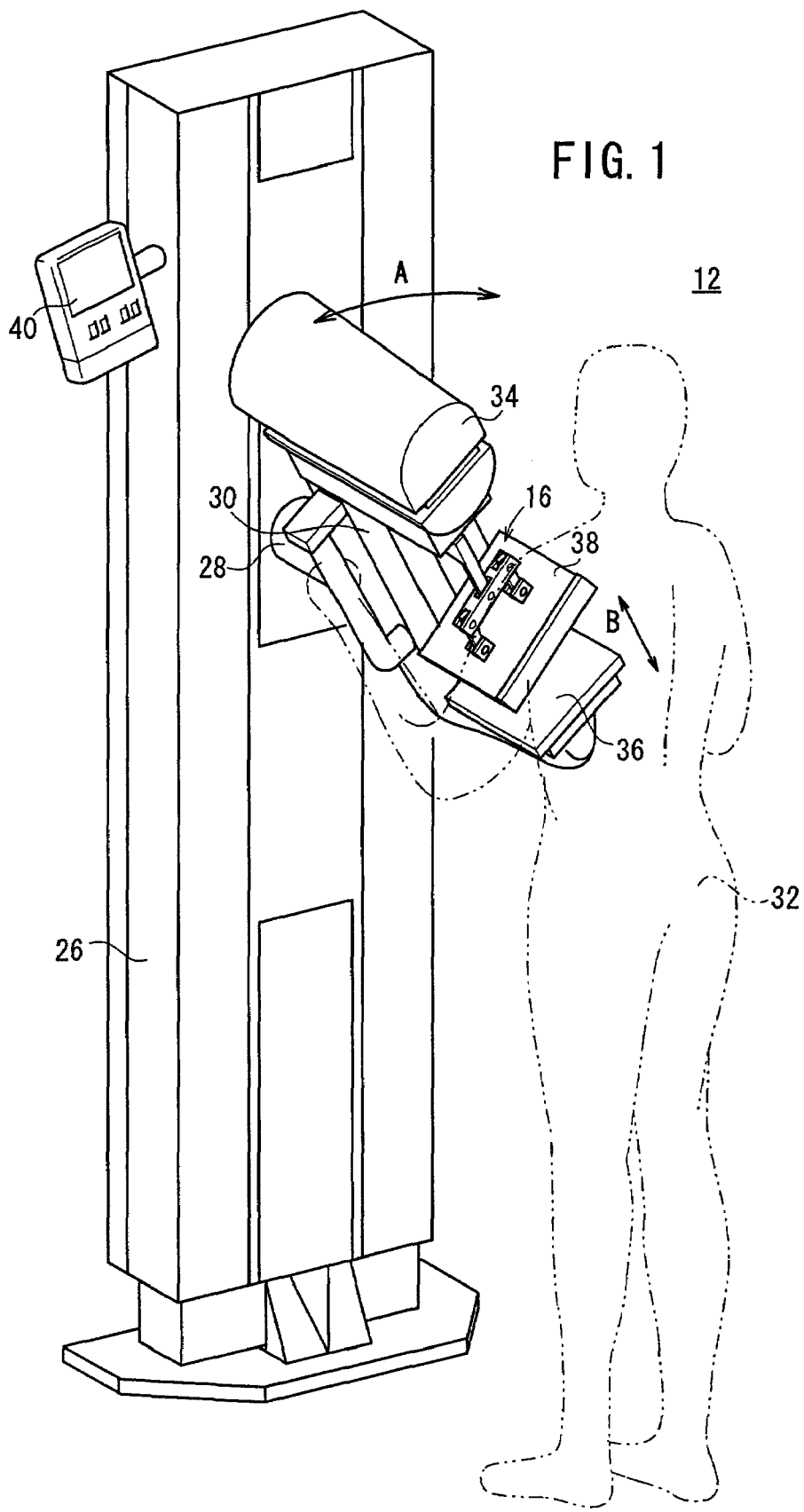
FIG. 1 is a perspective view of a mammographic apparatus according to an embodiment of the present invention.

FIG. 1 shows in perspective a mammographic apparatus 12 according to an embodiment of the present invention, the mammographic apparatus 12 incorporating a breast compression plate and a breast fixing method according to the present invention.

As shown in FIG. 1, the mammographic apparatus 12 includes an upstanding base 26, a vertical arm 30 fixed to a horizontal swing shaft 28 disposed substantially centrally on the base 26, a radiation source housing unit 34 housing a radiation source for applying a radiation to a breast 44 (see FIG. 3) to be imaged of a subject 32 and fixed to an upper end of the arm 30, an image capturing base 36 housing a solid-state detector for detecting a radiation that has passed through the breast 44 to acquire radiation image information of the breast 44 and fixed to a lower end of the arm 30, and a breast compression plate 38 for pressing and holding the breast 44 against the image capturing base 36.

To the base 26, there is connected a display control panel 40 for displaying image capturing information including an image capturing process to be performed by the mammographic apparatus 12, the ID information of the subject 32, etc., and setting these information, if necessary.

When the arm 30, to which the radiation source housing unit 34 and the image capturing base 36 are secured, is angularly moved about the swing shaft 28 in the directions indicated by the arrow A, an image capturing direction with respect to the breast 44 of the subject 32 is adjusted.

Figure 2:
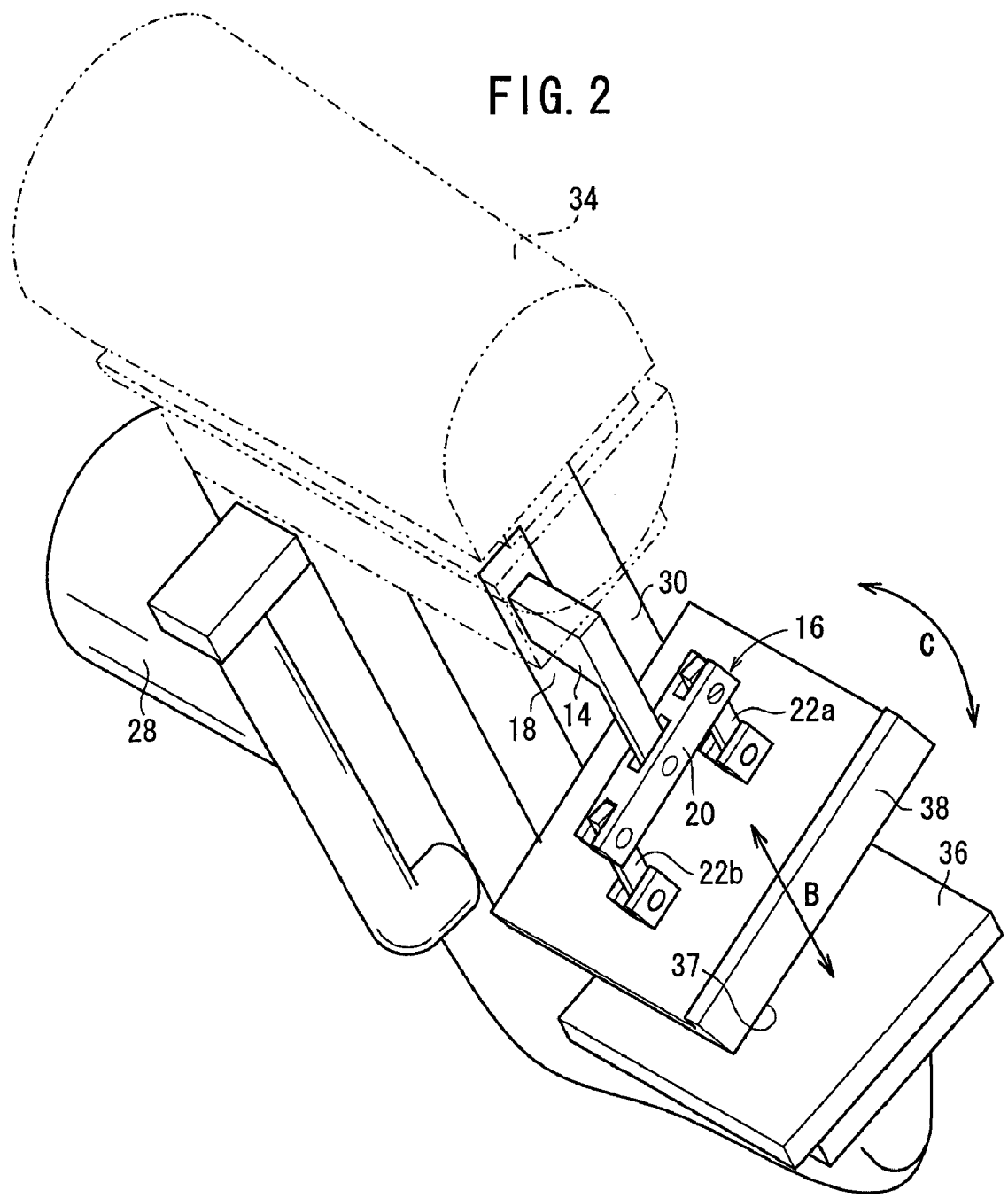
FIG. 2 is an enlarged perspective view of a compression plate support mechanism for swinging a breast compression plate of the mammographic apparatus according to the embodiment of the present invention.

As shown in FIG. 2, the breast compression plate 38 has a breast compression surface 37 integrally formed to provide a uniform transmittance for the radiation emitted from the radiation source. The breast compression plate 38 is disposed between the radiation source housing unit 34 and the image capturing base 36 and is coupled to the arm 30 by a compression plate support mechanism 16 (link mechanism). The compression plate support mechanism 16 includes a coupling member 14 movable along a groove 18 defined in the arm 30 for displacing the breast compression plate 38 in the directions indicated by the arrow B. The compression plate support mechanism 16 comprises a first link 20 having a central portion pivotally supported on the coupling member 14 and two second links 22a, 22b having ends pivotally supported on respective opposite ends of the first link 20 and other ends pivotally supported on the breast compression plate 38. The compression plate support mechanism 16 supports the breast compression plate 38 for angular movement in the directions indicated by the arrow C about an axis aligned with a straight line interconnecting the chest wall and the nipple of the breast 44 of the subject 32, as described later on.

The first link 20 is normally urged by, for example, a spring mounted on a pivot shaft between the first link 20 and the coupling member 14, to swing such that when there is no external force for the breast compression plate 38 to compress the breast 44, a portion of the breast compression surface 37 near the second links 22a is tilted away from the image capturing base 36 and an opposite portion of the breast compression surface 37 near the second links 22b is tilted toward the image capturing base 36.

Figure 3:
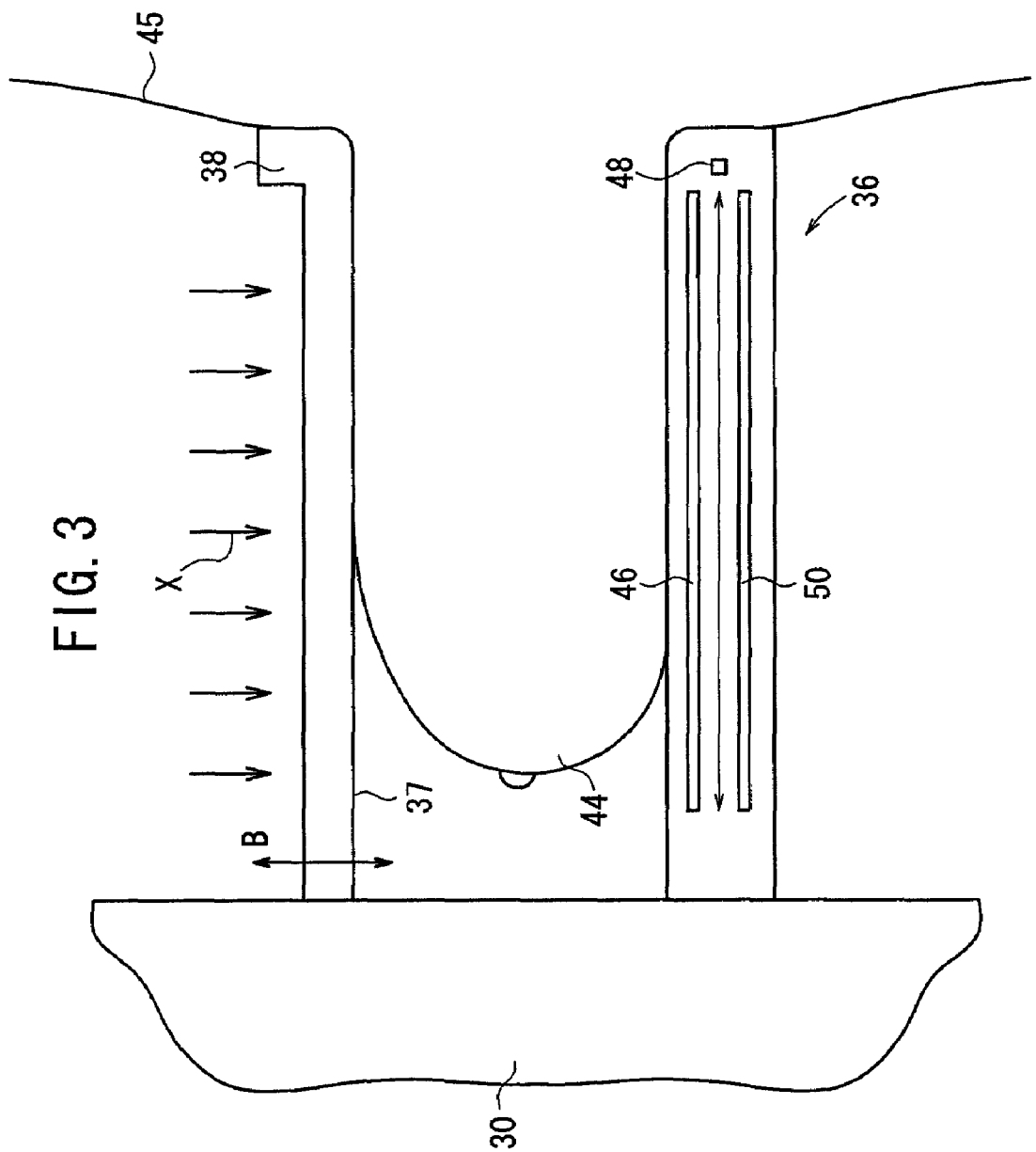
FIG. 3 is a fragmentary vertical elevational view, partly in cross section, showing internal structural details of an image capturing base of the mammographic apparatus according to the embodiment of the present invention.

FIG. 3 shows internal structural details of the image capturing base 36 of the mammographic apparatus 12. In FIG. 3, the breast 44 to be imaged of the subject 32 is shown as being placed between the image capturing base 36 and the breast compression plate 38. The reference numeral 45 represents the chest wall of the subject 32.

The image capturing base 36 houses therein a solid-state detector 46 (radiation image information detector) for storing radiation image information captured based on a radiation X that has been emitted from the radiation source stored in the radiation source housing unit 34 and has passed through the breast 44, and outputting the stored radiation image information as an electric signal, a reading light source 48 for applying reading light to the solid-state detector 46 to read the radiation image information stored in the solid-state detector 46, and an erasing light source 50 for applying erasing light to the solid-state detector 46 to remove unwanted electric charges stored in the solid state detector 46.

The solid-state detector 46 comprises a direct-conversion, light-reading radiation solid-state detector, for example. The solid-state detector 46 stores radiation image information based on the radiation X that has passed through the breast 44 as an electrostatic latent image, and generates an electric current depending on the electrostatic latent image when the solid-state detector 46 is scanned by the reading light applied from the reading light source 48.

The solid-state detector 46 may be a detector as disclosed in Japanese Laid-Open Patent Publication No. 2004-154409, for example. More specifically, the solid-state detector 46 comprises a laminated assembly of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer and which acts substantially as an electric conductor with respect to transport polarity charges which are of a polarity opposite to the latent image polarity electric charges, a reading photoconductive layer for generating electric charges and making itself electrically conductive upon exposure to the reading light, and a second electrically conductive layer which is permeable to the radiation X. An electric energy storage region is provided in the interface between the recording photoconductive layer and the charge transport layer.

Each of the first electrically conductive layer and the second electrically conductive layer provides an electrode. The electrode provided by the first electrically conductive layer comprises a two-dimensional flat electrode. The electrode provided by the second electrically conductive layer comprises a plurality of linear electrodes spaced at a predetermined pixel pitch for detecting the radiation image information to be recorded as an image signal. The linear electrodes are arranged in an array along a main scanning direction, and extend in an auxiliary scanning direction perpendicular to the main scanning direction.

The reading light source 48 includes, for example, a line light source comprising a linear array of LED chips and an optical system for applying a line of reading light emitted from the line light source to the solid-state detector 46. The linear array of LED chips extends perpendicularly to the direction in which the linear electrodes of the second electrically conductive layer of the solid-state detector 46 extend. The line light source moves along the directions, i.e., the directions indicated by the arrow, in which the linear electrodes extend to expose and scan the entire surface of the solid-state detector 46.

The erasing light source 50 comprises a plurality of LED chips which can emit and quench light in a short period of time and which have very short persistence.

The mammographic apparatus 12 according to the present embodiment is basically constructed as described above. Operation of the mammographic apparatus 12 will be described below.

Using a console, an ID card, etc., not shown, the operator or radiological technician sets the ID information of the subject 32, an image capturing process, etc. The ID information includes information as to the name, age, sex, etc. of the subject 32, and can be acquired from an ID card owned by the subject 32. If the mammographic apparatus 12 is connected to a network, then the ID information can be acquired from a higher-level apparatus through the network. The image capturing process includes information as to a region to be imaged, an image capturing direction, etc. instructed by the doctor, and can be acquired from a higher-level apparatus through the network or can be entered from the console by the radiological technician. The information can be displayed on the display control panel 40 of the mammographic apparatus 12.

Thereafter, the radiological technician places the mammographic apparatus 12 into a certain state according to the specified image capturing process. For example, the breast 44 may be imaged as a cranio-caudal view (CC) taken from above, a medio-lateral view (ML) taken outwardly from the center of the chest, or a medio-lateral oblique view (MLO) taken from an oblique view. Depending on information of a selected one of these image capturing processes, the radiological technician turns the arm 30 about the swing shaft 28.

A mode of operation of the mammographic apparatus 12 for taking a medio-lateral oblique view (MLO) of the breast 44 will be described below with reference to FIGS. 4 through 6.

Figure 4:
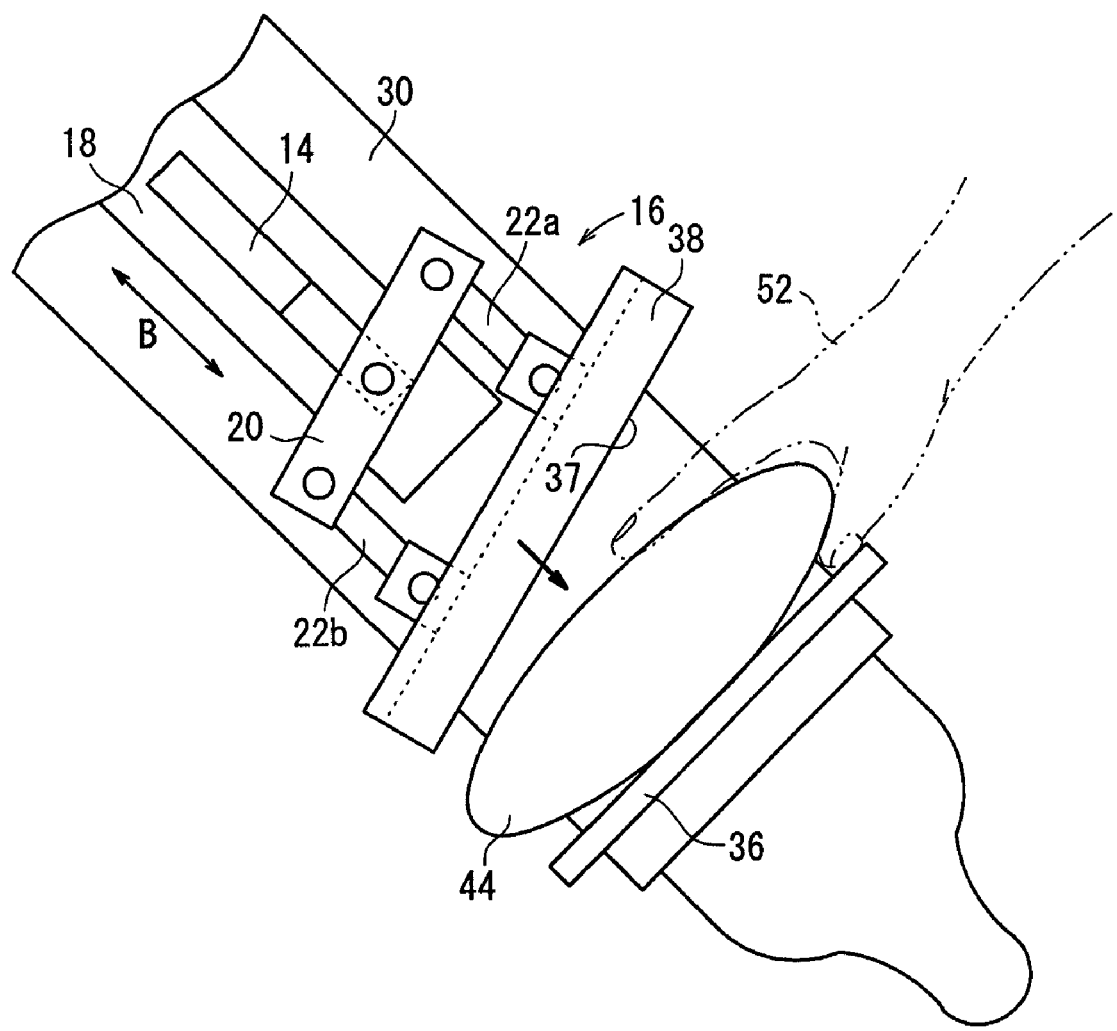
FIG. 4 is a side elevational view illustrative of a breast compression process performed in the mammographic apparatus according to the embodiment of the present invention.

After having placed the breast 44 in a certain position on the image capturing base 36, the radiological technician holds the breast 44 with a hand 52 and moves the breast compression plate 38 in the direction indicated by the arrow B, as shown in FIG. 4. The breast compression plate 38 moves, together with the compression plate support mechanism 16, toward the image capturing base 36.

Figure 5:
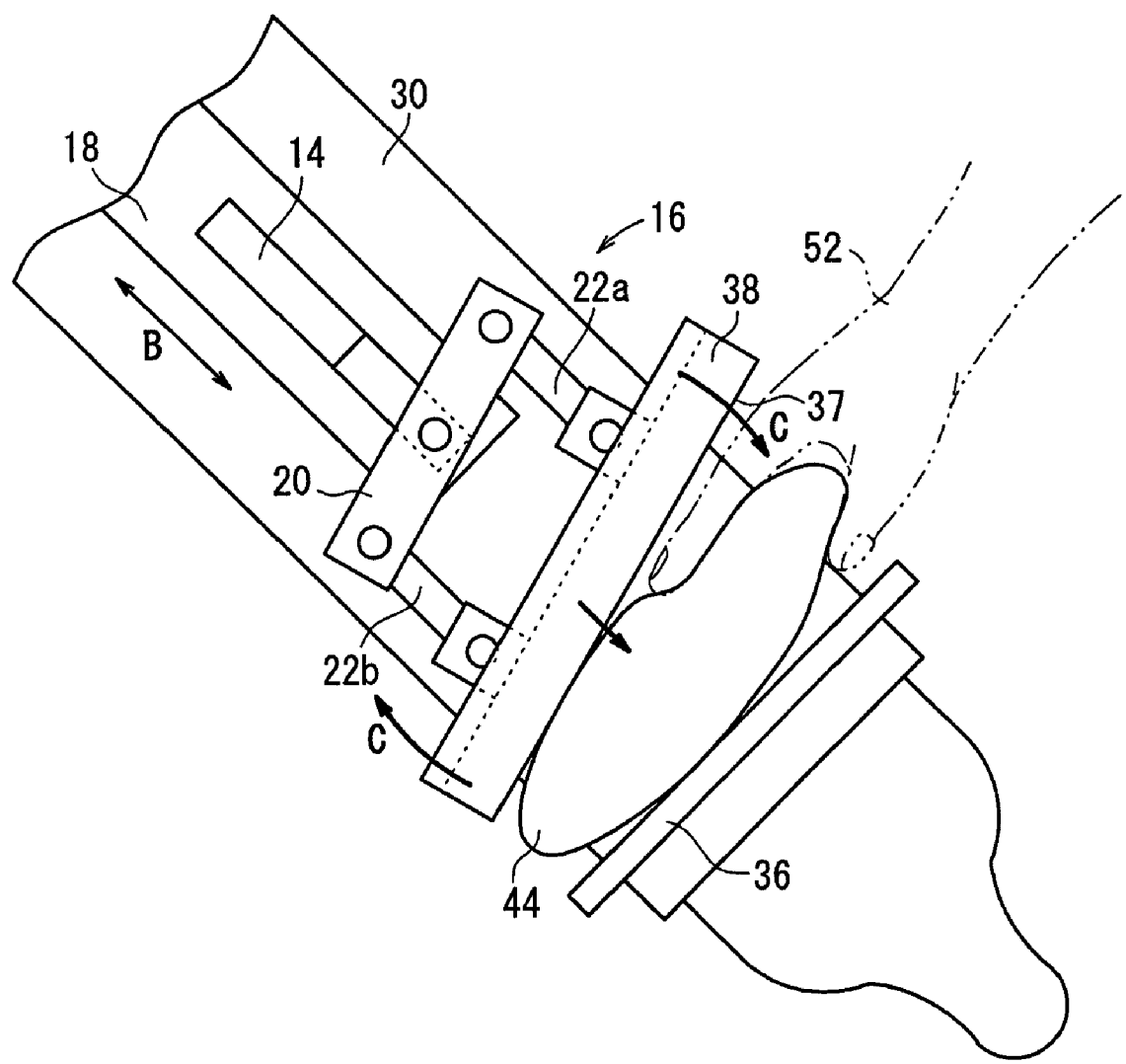
FIG. 5 is a side elevational view illustrative of the breast compression process performed in the mammographic apparatus according to the embodiment of the present invention.
Figure 6:
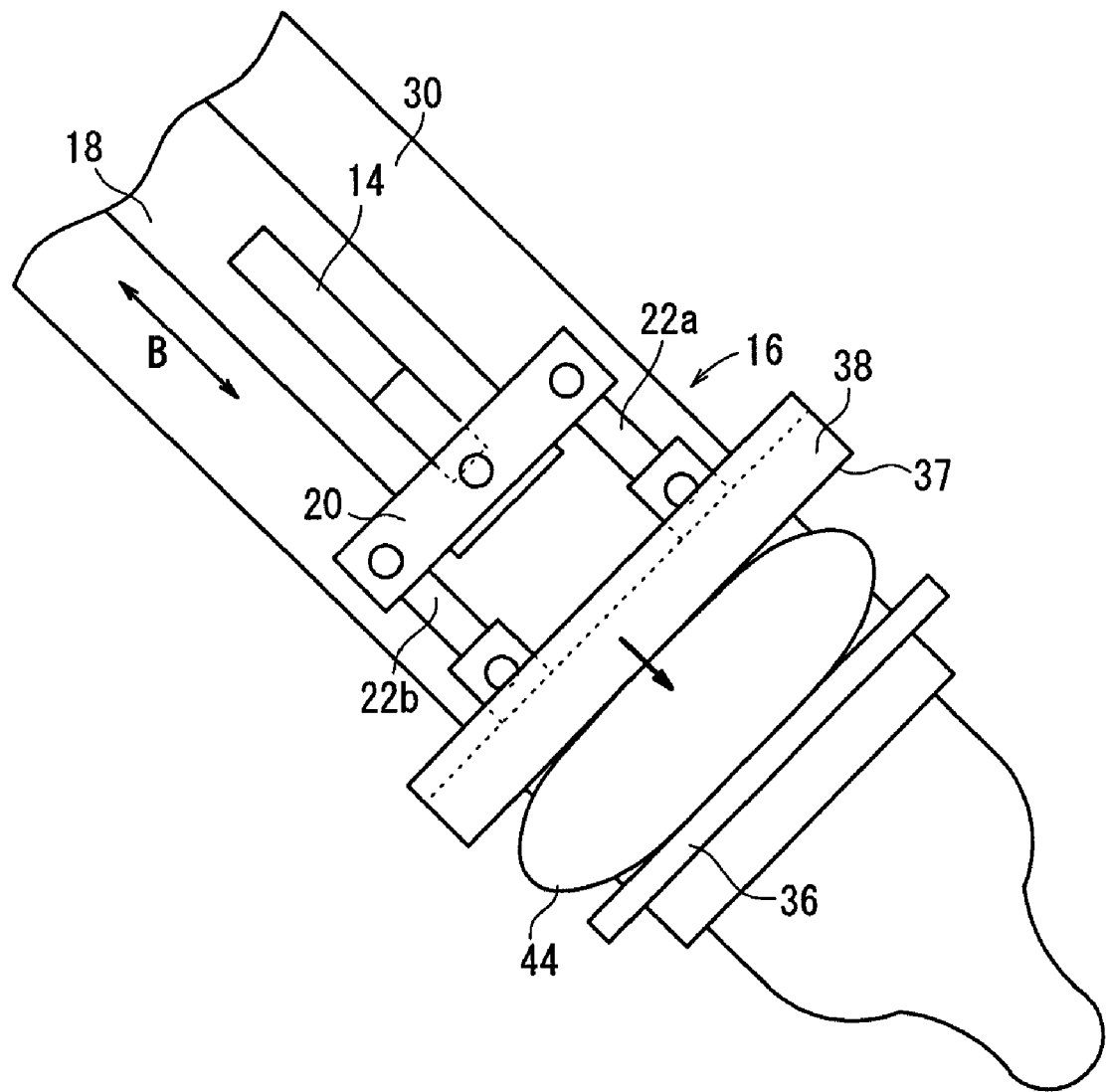
FIG. 6 is a side elevational view illustrative of the breast compression process performed in the mammographic apparatus according to the embodiment of the present invention.
Figure 7:
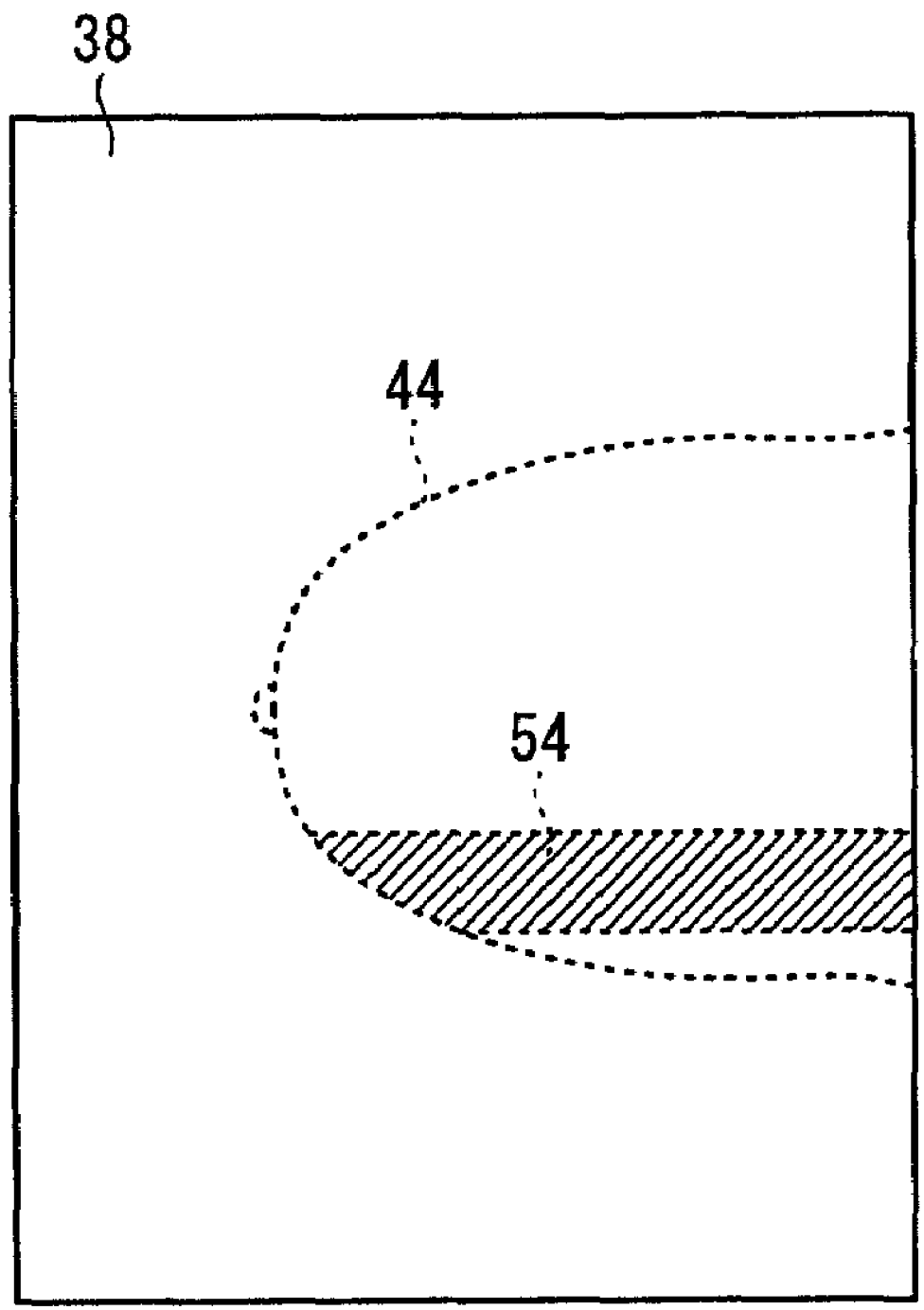
FIG. 7 is a view showing a compressed portion of a breast compressed by the breast compression plate which is in the breast compression process shown in FIG. 5.

When the breast compression plate 38 has moved a predetermined distance, the breast compression surface 37 of the breast compression plate 38 abuts against a portion, which is shown as a hatched region 54 in FIG. 7, of the breast 44, as shown in FIG. 5. Specifically, as shown in FIGS. 4 and 5, the breast compression plate 38 moves toward the image capturing base 36 such that the portion of the breast compression surface 37 near the second links 22a of the compression plate support mechanism 16 is tilted away from the image capturing base 36 and the opposite portion of the breast compression surface 37 near the second links 22b is tilted toward the image capturing base 36. First, the breast compression plate 38 abuts against a lower portion of the breast 44 in the direction of gravitational force.

Figure 17:
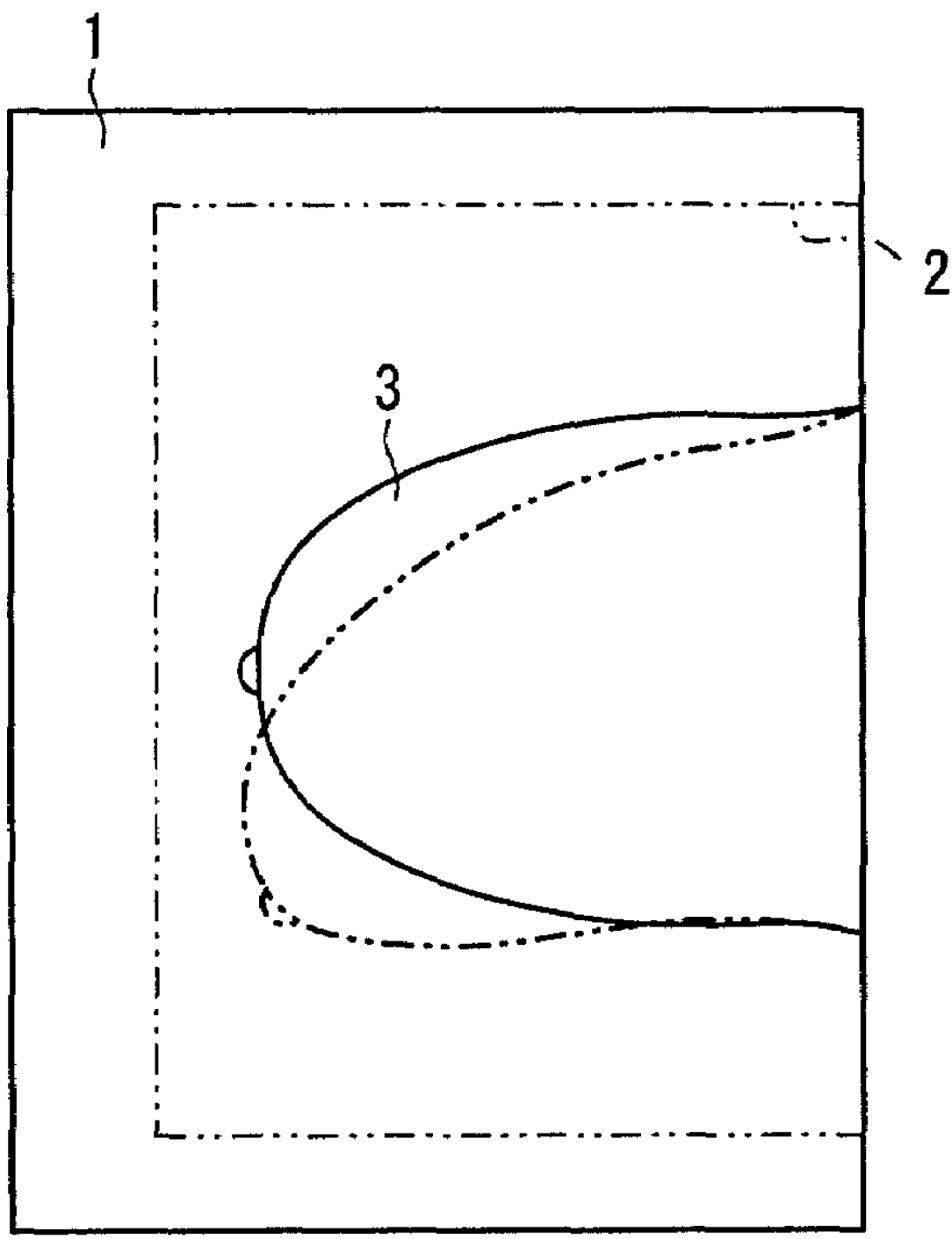
FIG. 17 is a view illustrative of the manner in which a breast is fixed by a breast compression plate of the conventional art.

The hatched region 54 of the breast 44 which abuts the breast compression surface 37 is positioned below a straight line interconnecting the chest wall 45 and the nipple of the breast 44 in the direction of gravitational force. As the radiological technician is holding the breast 44 with the hand 52, the portion of the breast 44 near the nipple does not droop due to the weight of the breast 44, unlike the condition shown in FIG. 17.

After the breast compression surface 37 abuts against the hatched region 54 of the breast 44, the radiological technician removes the hand 52 from the gap between the image capturing base 36 and the breast compression plate 38. At this time, since a portion of the breast 44 which ranges from the chest wall 45 to the nipple is braced from below, the breast 44 is prevented from being displaced in position upon removal of the hand 52. Furthermore, the radiological technician can easily remove the hand 52 from the gap between the image capturing base 36 and the breast compression plate 38 without allowing the breast 44 from being displaced in position because the breast compression plate 38 is tilted away from the image capturing base 36 over the gap where the hand 52 is inserted.

After having pulled out the hand 52, the radiological technician further moves the breast compression plate 38 toward the image capturing base 36. The breast compression plate 38 is now turned about the hatched region 54 of the breast 44 abutted against the breast compression surface 37 in the direction indicated by the arrow C (FIG. 5) until the breast compression plate 38 becomes substantially parallel to the image capturing base 36. The breast compression plate 38 now compresses the breast 44 through a wide area of the breast compression surface 37, as shown in FIG. 6.

After the breast 44 has thus been positioned between the image capturing base 36 and the breast compression plate 38, the mammographic apparatus 12 starts capturing an image of the breast 44.

The radiation X emitted from the radiation source housed in the radiation source housing unit 34 is applied through the breast compression plate 38 to the breast 44. The radiation X that has passed through the breast 44 is detected by the solid-state detector 46 housed in the image capturing base 36, by which radiation image information of the breast 44 is recorded. After the radiation image information of the breast 44 is captured, the reading light source 48 moves in the direction indicated by the arrow (FIG. 3) along the solid-state detector 46 to read the radiation image information recorded in the solid-state detector 46. The solid-state detector 46 from which the radiation image information has been read is irradiated with erasing light emitted from the erasing light source 50 to remove unwanted electric charges stored in the solid-state detector 46. The solid-state detector 46 is now ready to record next radiation image information.

The mode of operation of the mammographic apparatus 12 for taking a medio-lateral oblique view (MLO) of the breast 44 has been described above. When the mammographic apparatus 12 is set to take a medio-lateral view (ML) of the breast 44, since the lower portion (the hatched region 54 in FIG. 7) of the breast 44 is also supported by the breast compression surface 37 of the breast compression plate 38 that is tilted with respect to the image capturing base 36, the breast 44 can be positioned easily and highly accurately with respect to the image capturing base 36. When the mammographic apparatus 12 is set to take a cranio-caudal view (CC) of the breast 44, as the large gap is created between the image capturing base 36 and the breast compression plate 38, as shown in FIG. 5, the radiological technician finds it easy to remove the hand 52 from the gap after having compressed the breast compression surface 37 against the breast 44.

Figure 8:
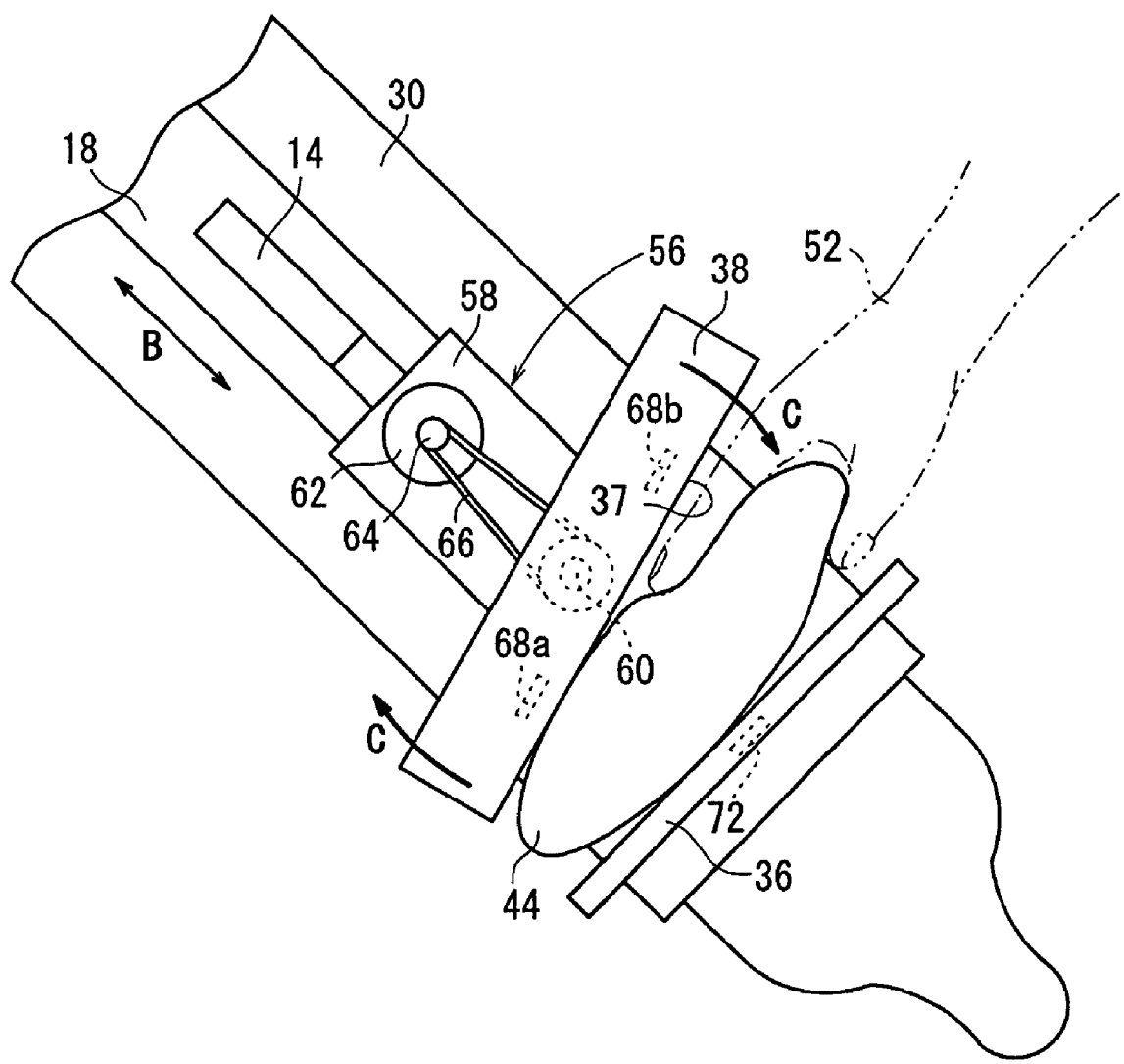
FIG. 8 is a side elevational view of a compression plate support mechanism for turning a breast compression plate in a mammographic apparatus according to another embodiment of the present invention.

Instead of the compression plate support mechanism 16 used in the link mechanism as shown in FIG. 1, FIG. 8 shows in side elevation a compression plate support mechanism 56 supporting the breast compression plate 38 and including a compression plate turning motor 62 (turning means) for angularly moving the breast compression plate 38 in the direction indicated by the arrow C. The breast compression plate 38 is angularly movably supported on a bracket 58 connected to the coupling member 14 by a pivot shaft 60. The compression plate turning motor 62 is fixedly mounted on the bracket 58 and has a drive shaft 64 that is operatively connected to the pivot shaft 60 by an endless belt 66.

The breast compression plate 38 as it is tilted a certain angle with respect to the image capturing base 36 is moved toward the image capturing base 36. After the breast compression plate 38 abuts a portion of the breast 44 on the image capturing base 36, the compression plate turning motor 62 is energized to turn the breast compression plate 38 in the direction indicated by the arrow C to press and hold the breast 44 between the image capturing base 36 and the breast compression plate 38.

Figure 9:
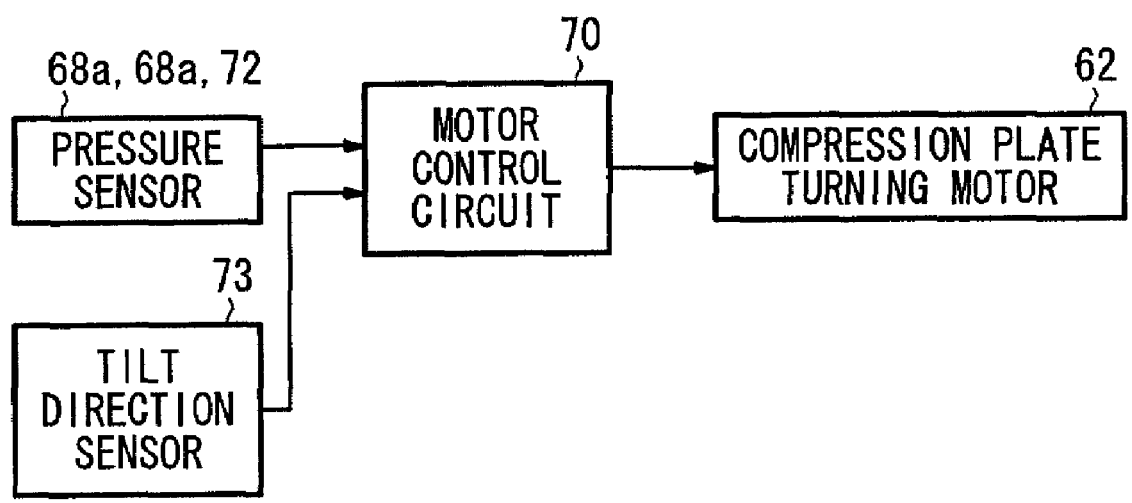
FIG. 9 is a block diagram of a timing control circuit for turning a breast compression plate.

A timing control circuit shown in FIG. 9 serves to adjust a tilt angle of the breast compression plate 38 before it compresses the breast 44 and also to perform timing control for turning the breast compression plate 38 in the direction indicated by the arrow C after the breast compression surface 37 abuts against the breast 44.

As shown in FIG. 9, the timing control circuit includes pressure sensors 68a, 68b (timing detecting means) disposed in portions of the compression surface 37 for initially compressing the breast 44, and a tilt direction sensor 73 (tilt direction detecting means) disposed in the image capturing base 36 for detecting a direction in which the image capturing base 36 is tilted with respect to the horizontal direction. The tilt direction sensor 73 may be disposed in the arm 30 or the swing shaft 28.

The timing control circuit also includes a motor control circuit 70 (support mechanism drive means) for determining one of the directions indicated by the arrow A (FIG. 1) in which the image capturing base 36 is tilted, from the tilt direction detected by the tilt direction sensor 73, and energizing the compression plate turning motor 62 according to the determined direction to tilt the breast compression plate 38 in the direction with respect to the image capturing base 36. For example, if the image capturing base 36 is inclined in the direction shown in FIG. 8, then the motor control circuit 70 controls the compression plate turning motor 62 to turn and tilt the breast compression plate 38 so that the breast compression plate 38 approaches a lower portion of the image capturing base 36 as it is tilted and is spaced from an upper portion of the image capturing base 36 as it is tilted. Conversely, if the image capturing base 36 is inclined in the direction opposite to the direction shown in FIG. 8, then the motor control circuit 70 controls the compression plate turning motor 62 to turn and tilt the breast compression plate 38 in the direction opposite to the above direction.

After the motor control circuit 70 has thus tilted the breast compression plate 38, the compression plate turning motor 62 is moved toward the image capturing base 36. The motor control circuit 70 monitors a pressure detected by one of the pressure sensors 68a, 68b. For example, if the breast compression plate 38 is tilted as shown in FIG. 8, then the motor control circuit 70 monitors a pressure detected by the pressure sensor 68a.

Figure 10:
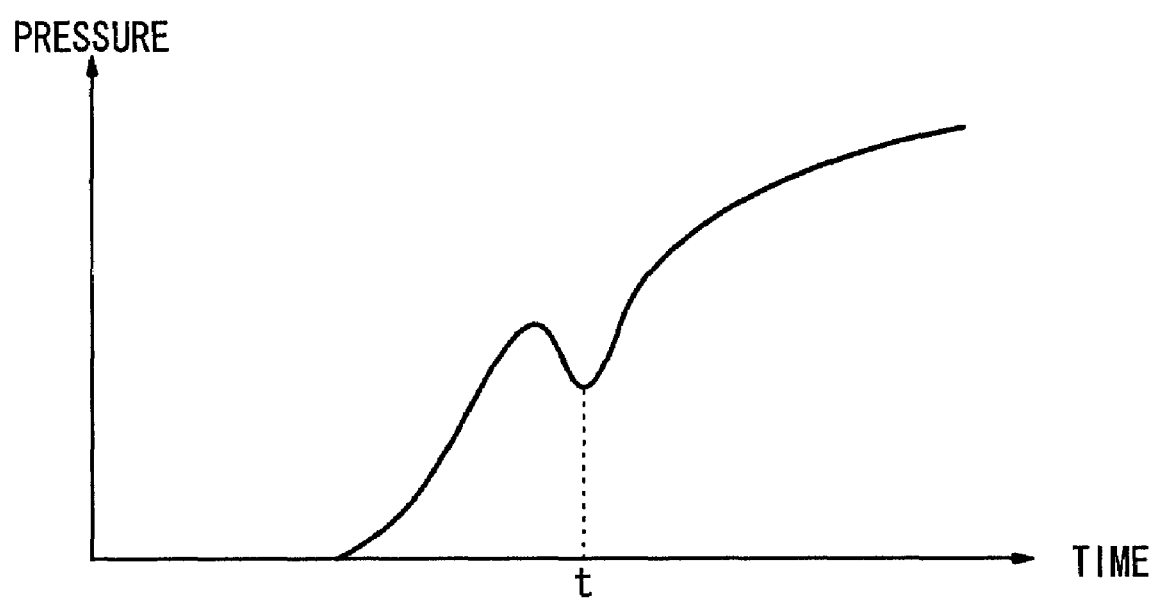
FIG. 10 is a graph showing the characteristic curve of a pressure detected by a pressure sensor of the timing circuit shown in FIG. 9.

As shown in FIG. 10, the pressure detected by each of the pressure sensors becomes greater when the breast compression plate 38 is moved toward the image capturing base 36 and compresses the breast 44. When the radiological technician removes the hand 52 which has held the breast 44 from between the image capturing base 36 and the breast compression plate 38, the pressure temporarily drops at time t in FIG. 10. If the motor control circuit 70 detects a certain change in the pressure that is detected by the pressure sensor 68 and monitored by the motor control circuit 70, then the motor control circuit 70 controls the compression plate turning motor 62 to turn the breast compression plate 38 to make it parallel to the image capturing base 36. Accordingly, the breast compression plate 38 can be turned in timed relation to the removal of the hand 52 from between the image capturing base 36 and the breast compression plate 38, thereby positioning the breast 44 in a desired state between the image capturing base 36 and the breast compression plate 38.

As shown in FIG. 8, a pressure sensor 72 may be disposed in the portion of the image capturing base 36 on which the breast 44 is to be positioned, and the motor control circuit 70 may control the compression plate turning motor 62 based on a pressure detected by the pressure sensor 72.

Figure 11:
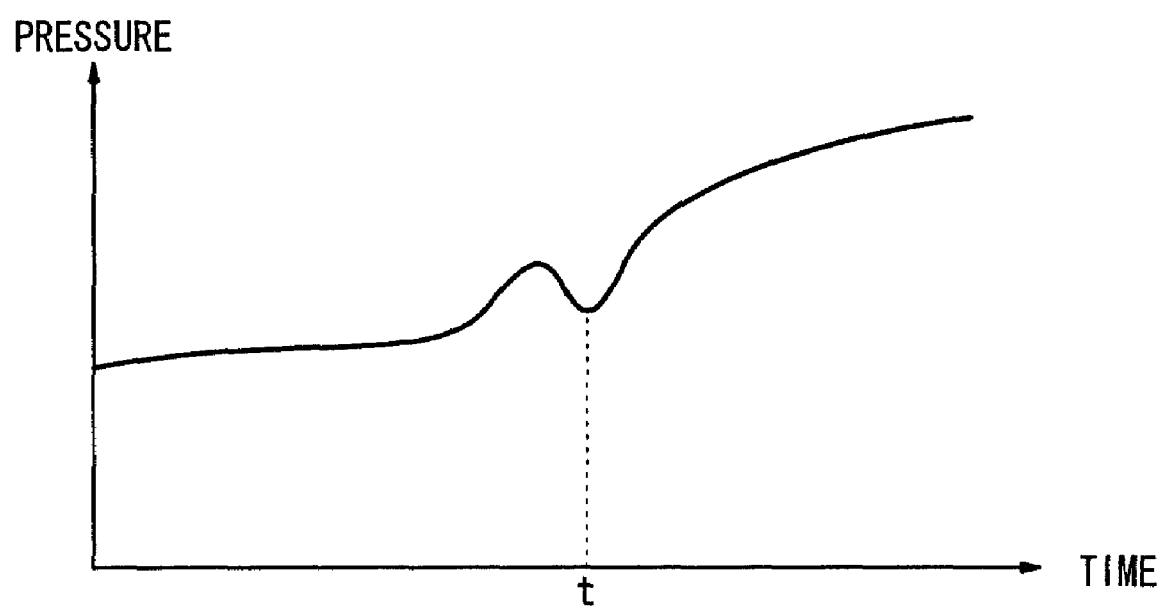
FIG. 11 is a graph showing the characteristic curve of a pressure detected by another pressure sensor for use in the timing circuit shown in FIG. 9.

As shown in FIG. 11, the pressure detected by the pressure sensor 72 has a certain pressure level even before the breast compression plate 38 abuts against the breast 44 because of the weight of the breast 44 and the pressure that is applied to the breast 44 by the hand 52 of the radiological technician for positioning the breast 44. After the breast compression plate 38 has abutted the breast 44, the pressure sensor 72 detects a pressure drop when the radiological technician pulls out the hand 52, and the motor control circuit 70 controls the compression plate turning motor 62 to turn the breast compression plate 38, thereby positioning the breast 44 in a desired state between the image capturing base 36 and the breast compression plate 38.

Figure 12:
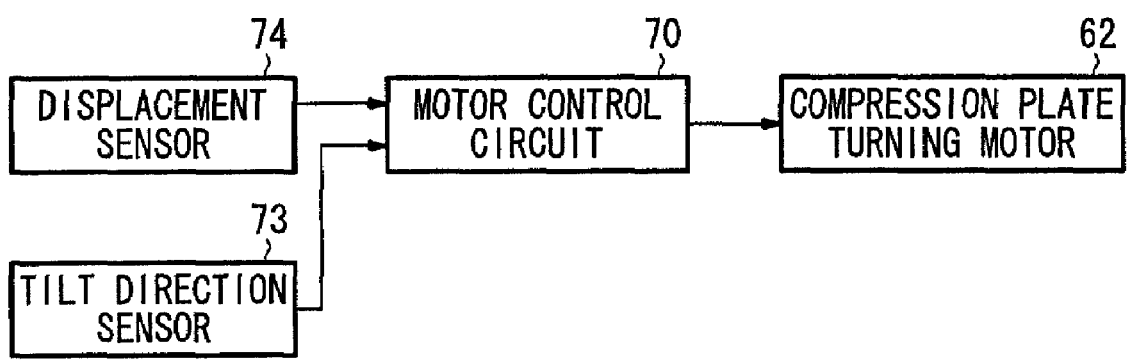
FIG. 12 is a block diagram of a timing control circuit for turning a breast compression plate according to still another embodiment of the present invention.

FIG. 12 shows in block form another timing control circuit. The timing control circuit shown in FIG. 12 includes a displacement sensor 74 connected to the breast compression plate 38 for detecting a displacement of the breast compression plate 38 that moves with respect to the image capturing base 36. When the displacement sensor 74 detects a certain displacement of the breast compression plate 38, the motor control circuit 70 controls the compression plate turning motor 62 to turn the breast compression plate 38 to make it parallel to the image capturing base 36.

In the above embodiments, the breast compression plate 38 is turned at a time that is automatically adjusted based on the pressure detected by the pressure sensors 68a, 68b or the displacement detected by the displacement sensor 74. However, the breast compression plate 38 may be turned by a manual switch which is operated by the radiological technician.

Figure 13:
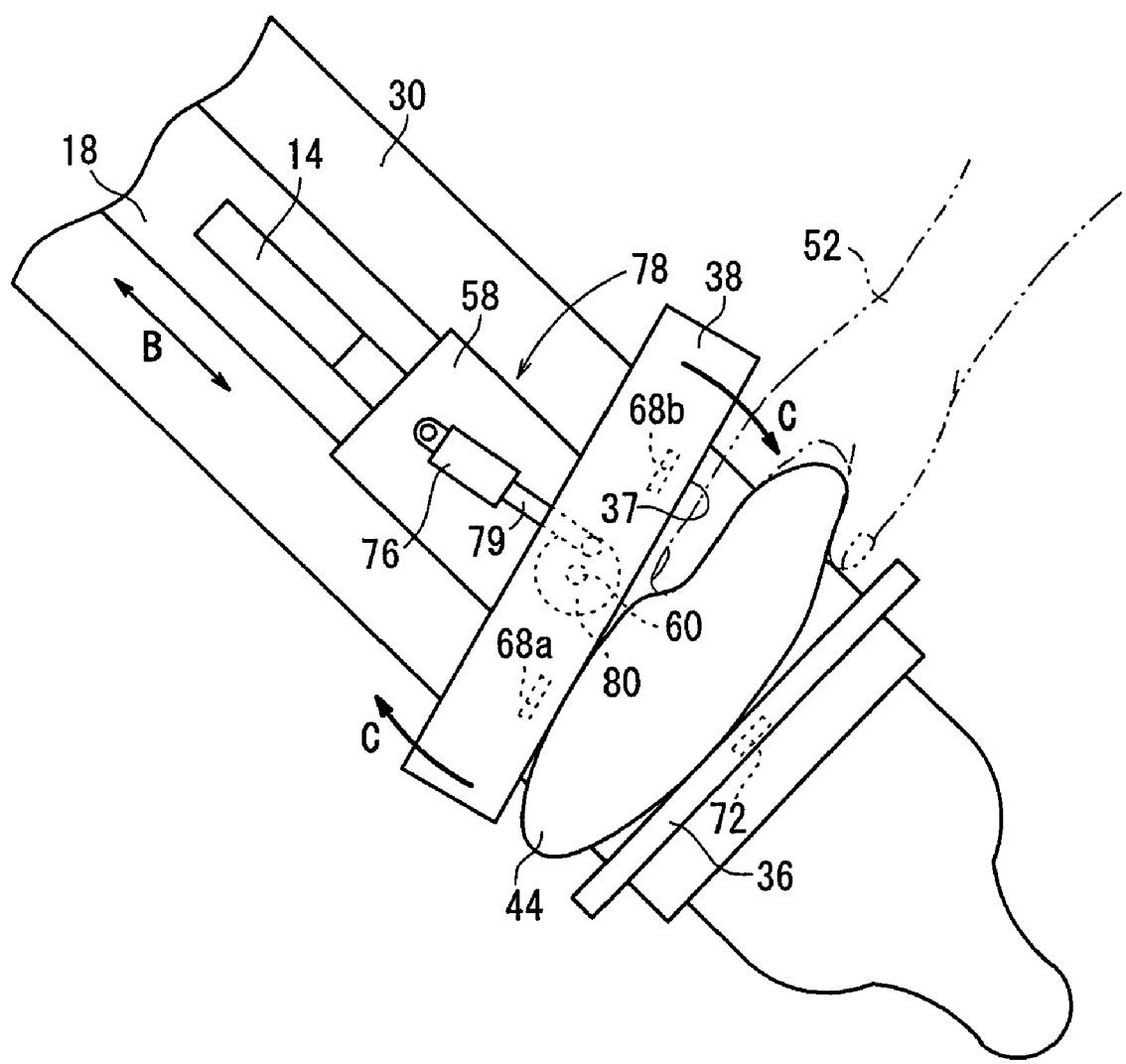
FIG. 13 is a side elevational view of a compression plate support mechanism for turning a breast compression plate according to still another embodiment of the present invention.

Instead of the compression plate turning motor 62 shown in FIG. 8, FIG. 13 shows a compression plate support mechanism 78 including an air cylinder 76 according to still another embodiment of the present invention. As shown in FIG. 13, the air cylinder 76 has an end pivotally supported on the bracket 58 and a piston rod 79 projecting from the other end and pivotally supported off-center on a rotor 80 that is fixed to the pivot shaft 60 of the breast compression plate 38.

When the pressure sensors 68a, 68b or the pressure sensor 72 detects a certain pressure change, the air cylinder 76 is actuated to turn the rotor 80 for thereby turning the breast compression plate 38 to make it parallel to the image capturing base 36.

Figure 14:
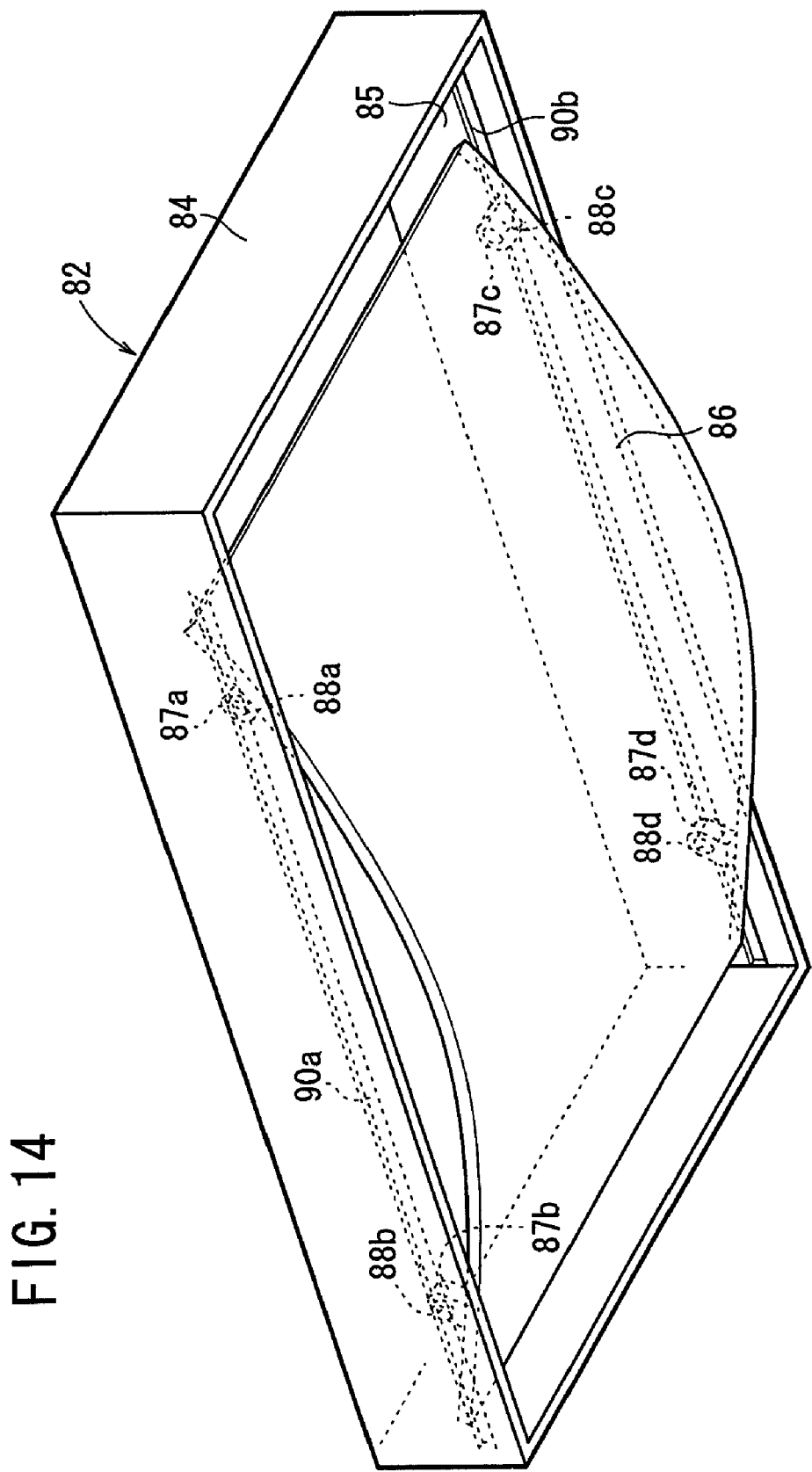
FIG. 14 is a perspective view of a compression plate support mechanism for turning a breast compression plate according to yet another embodiment of the present invention.

FIG. 14 shows a compression plate support mechanism 82 according to yet another embodiment of the present invention. As shown in FIG. 14, the compression plate support mechanism 82 comprises a casing 84 and a flexibly curved breast compression plate 86 disposed in an opening 85 in the casing 84. The breast compression plate 86 includes a curved portion projecting from the casing 84 for abutting contact with the portion of the breast 44 which extends from the chest wall 45 to the nipple. The breast compression plate 86 has pins 88a through 88d disposed in respective brackets 87a through 87d that are mounted on opposite side edges of the breast compression plate 86. The pins 88a through 88d engage in grooves 90a, 90b defined in opposite inner side wall surfaces of the casing 84 for sliding movement along the grooves 90a, 90b.

Figure 15:
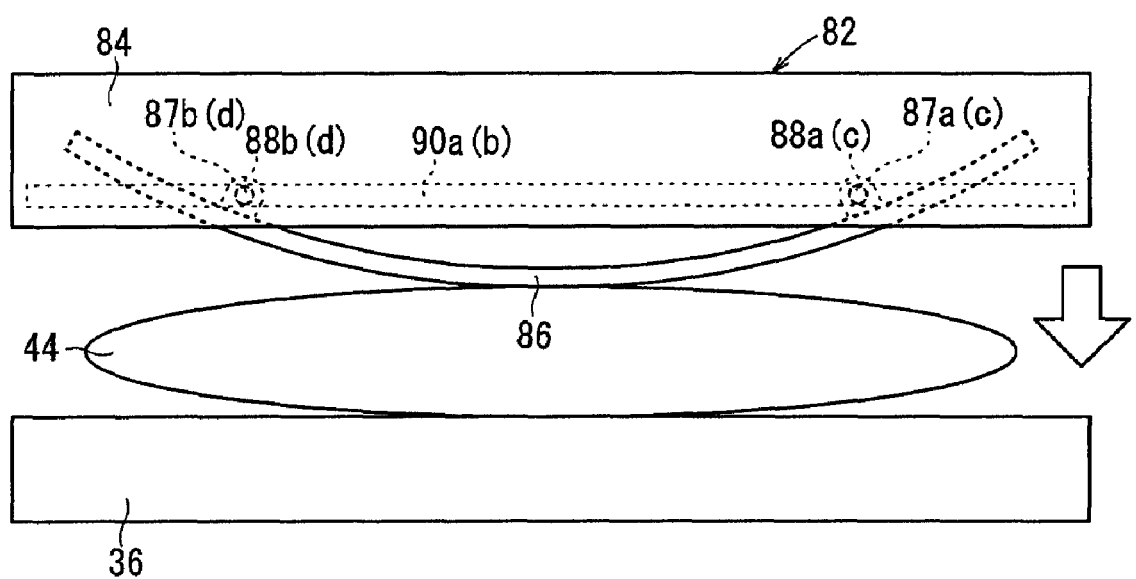
FIG. 15 is a front elevational view illustrative of the manner in which the breast compression plate shown in FIG. 14 compresses a breast.
Figure 16:
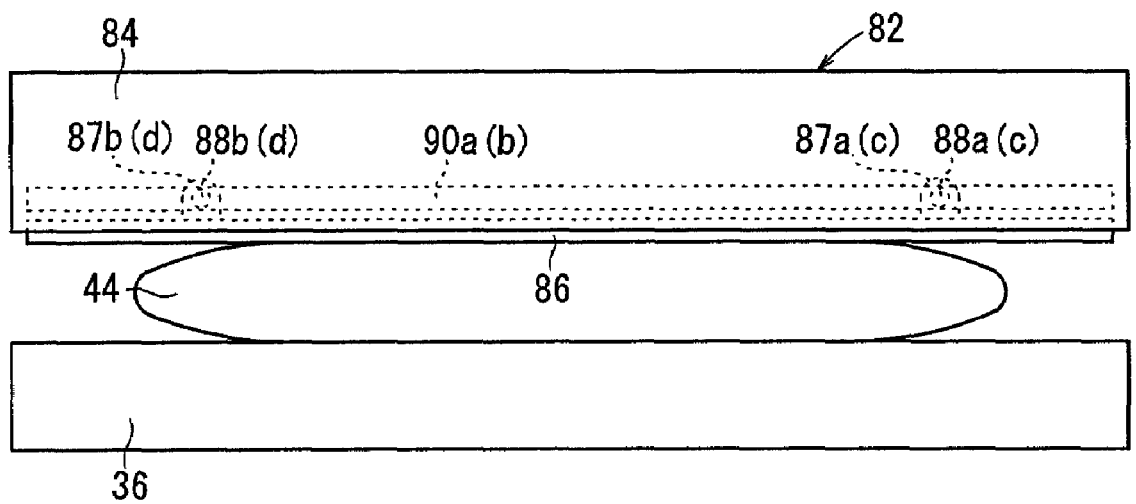
FIG. 16 is a front elevational view illustrative of the manner in which the breast compression plate shown in FIG. 14 compresses the breast.

When the compression plate support mechanism 82 is moved a certain distance toward the image capturing base 36, as shown in FIG. 15, the central area of the projecting portion of the breast compression plate 86 abuts against a part of the breast 44 from the chest wall 45 to the nipple, thereby positioning the breast 44 on the image capturing base 36. Then, the radiological technician removes the hand 52 from between the image capturing base 36 and the breast compression plate 38, and further moves the breast compression plate 38 toward the image capturing base 36. At this time, the central area of the projecting portion of the breast compression plate 86 is pressed toward the casing 84 under reactive forces from the breast 44. As a result, as shown in FIG. 16, the breast compression plate 86 becomes flat, thereby securely positioning the breast 44 in a desired state between the image capturing base 36 and the breast compression plate 38.

The mammographic apparatus 12 in the illustrated embodiments employ the solid-state detector 46 for storing radiation image information. However, the present invention is also applicable to a mammographic apparatus which employs a stimulable phosphor panel for storing radiation image information.

Although certain preferred embodiments of the present invention have been shown and described in detail, it should be understood that various changes and modifications may be made therein without departing from the scope of the appended claims.

What is claimed is:

1. A mammographic apparatus comprising:
    a radiation source for applying a radiation to a breast of a subject;
    an image capturing base including a radiation image information detector for detecting the radiation which has passed through said breast to capture radiation image information of said breast;
    a breast compression plate including a breast compression surface movable toward and away from said image capturing base, for compressing said breast against said image capturing base with said breast compression surface;
    said breast compression surface including a first compression portion of a predetermined range continuously extending in a direction from a chest wall of the subject to a nipple of said breast and a second compression portion disposed substantially perpendicularly to said direction from said first compression portion;
    a compression plate support mechanism supporting said breast compression plate such that said first compression portion is closer to said image capturing base than said second compression portion;
    wherein said compression plate support mechanism supports said breast compression plate with said breast compression surface being tilted with respect to said image capturing base; and
    wherein said compression plate support mechanism supports said breast compression plate so as to be tilted with said first compression portion being positioned vertically below said second compression portion when said image capturing base is tilted with respect to the horizontal direction.

2. A mammographic apparatus according to claim 1, wherein said breast compression surface is integrally formed to provide a uniform transmittance for the radiation emitted from said radiation source.

3. A mammographic apparatus according to claim 1, further comprising:
    tilt direction detecting means for detecting a direction in which said image capturing base is tilted with respect to the horizontal direction;
    wherein said compression plate support mechanism supports said breast compression plate so as to be tilted with said first compression portion being positioned vertically below said second compression portion, based on the direction detected by said tilt direction detecting means.

4. A mammographic apparatus according to claim 1, wherein said compression plate support mechanism supports said breast compression plate with said first compression portion projecting and being curved with respect to said image capturing plate.

5. A mammographic apparatus according to claim 1, wherein said compression plate support mechanism supports said breast compression plate with said first and second compression portions being changed to a predetermined attitude for pressing said breast when said breast is pressed against said image capturing base.

6. A mammographic apparatus according to claim 5, wherein said compression plate support mechanism comprises a link mechanism for supporting said breast compression plate swingably to change said first and second compression portions to a predetermined attitude for pressing said breast.

7. A mammographic apparatus according to claim 5, wherein said compression plate support mechanism comprises turning means for supporting said breast compression plate swingably to change said first and second compression portions to a predetermined attitude for pressing said breast.

8. A mammographic apparatus according to claim 7, wherein said compression plate support mechanism supports said breast compression plate rotatably with respect to said image capturing base for rotation about an axis along the direction from the chest wall of the subject to the nipple of said breast.

9. A mammographic apparatus according to claim 5, wherein said compression plate support mechanism supports said breast compression plate with said first compression portion projecting and being curved with respect to said image capturing plate, and also supports said breast compression plate such that when said breast compression plate presses said breast against said image capturing base, said breast compression plate is deformed under reactive forces from said breast to move said first and second compression portions to a predetermined position for pressing said breast.

10. A mammographic apparatus according to claim 9, wherein said compression plate support mechanism includes at least two rotational shafts along the direction from the chest wall of the subject to the nipple of said breast, and supports said breast compression plate with said rotational shafts rotatably with respect to said image capturing base.

11. A mammographic apparatus according to claim 5, wherein said breast compression plate or said image capturing base includes timing detecting means for detecting a time to change the attitude of said breast compression surface for causing said second compression portion to press said breast.

12. A mammographic apparatus according to claim 11, wherein said timing detecting means comprises a pressure sensor for detecting a predetermined pressure under which said breast is pressed by said breast compression surface, and changes the attitude of said breast compression surface based on a time at which said predetermined pressure is detected by said pressure sensor.

13. A mammographic apparatus according to claim 12, further comprising:
support mechanism drive means for actuating said compression plate support mechanism based on a time at which the pressure detected by said pressure sensor changes from an increasing tendency to a decreasing tendency, thereby to change the attitude of said breast compression surface.

14. A mammographic apparatus according to claim 11, wherein said timing detecting means comprises a displacement sensor for detecting a predetermined displacement of said breast compression plate with respect to said image capturing base, and changes the attitude of said breast compression surface based on a time at which said predetermined displacement is detected by said displacement sensor.

15. A mammographic apparatus according to claim 1, wherein said compression plate support mechanism includes at least two rotational shafts along the direction from the chest wall of the subject to the nipple of said breast, and supports said breast compression plate with said rotational shafts rotatably with respect to said image capturing base.

16. A mammographic apparatus according to claim 1, wherein said tilting occurs at time of said image capture.

17. A breast compression plate in a mammographic apparatus for applying a radiation to a breast of a subject to capture radiation image information of said breast, wherein said breast compression plate includes a breast compression surface movable toward and away from an image capturing base, for compressing said breast against said image capturing base with said breast compression surface;
said breast compression surface including a first compression portion of a predetermined range continuously extending in a direction from a chest wall of the subject to a nipple of said breast and a second compression portion disposed substantially perpendicularly to said direction; and
a compression plate support mechanism supports said breast compression plate with said breast compression surface being tilted during image capture with respect to said image capturing base; and
wherein said first compression portion is closer to said image capturing base than said second compression portion; and
wherein said compression plate support mechanism supports said breast compression plate so as to be tilted with said first compression portion being positioned vertically below said second compression portion when said image capturing base is tilted with respect to the horizontal direction.

18. A method of fixing a breast of a subject to an image capturing base in a mammographic apparatus, with a breast compression plate including a breast compression surface including a first compression portion of a predetermined range continuously extending in a direction from a chest wall of the subject to a nipple of said breast and a second compression portion disposed substantially perpendicularly to said direction, said method comprising the steps of:
placing the breast in a predetermined position on the image capturing base;
pressing said breast compression plate against said breast such that said first compression portion is closer to said image capturing base than said second compression portion;
wherein a compression plate support mechanism supports said breast compression plate with said breast compression surface being tilted with respect to said image capturing base at image capture; and
wherein said compression plate support mechanism supports said breast compression plate so as to be tilted with said first compression portion being positioned vertically below said second compression portion when said image capturing base is tilted with respect to the horizontal direction.

* * * * *